United States Patent [19]

Okamoto et al.

[11] Patent Number: 5,688,526
[45] Date of Patent: Nov. 18, 1997

[54] HEMOGLOBIN-ENCAPSULATING LIPOSOME AND METHOD FOR MAKING THE SAME

[75] Inventors: Takeshi Okamoto; Hiroshi Goto, both of Kanagawa, Japan

[73] Assignee: Terumo Kabushiki Kaisha, Shibuya-ku, Japan

[21] Appl. No.: 565,937

[22] Filed: Dec. 1, 1995

Related U.S. Application Data

[63] Continuation of Ser. No. 214,133, Mar. 16, 1994, abandoned.

[30] Foreign Application Priority Data

Mar. 18, 1993  [JP]  Japan ........................... 5-59067

[51] Int. Cl.⁶ .................................................. A61K 9/127
[52] U.S. Cl. ..................................................... 424/450
[58] Field of Search .............................................. 424/450

[56] References Cited

U.S. PATENT DOCUMENTS

| | | | |
|---|---|---|---|
| 4,133,874 | 1/1979 | Miller | 424/38 |
| 4,321,259 | 3/1982 | Nicolau | 424/101 |
| 4,376,059 | 3/1983 | Davis | 424/450 |
| 4,439,357 | 3/1984 | Bonhard | 424/101 |
| 5,039,665 | 8/1991 | Markov | 514/23 |

FOREIGN PATENT DOCUMENTS

| | | |
|---|---|---|
| 0 158 684 | 10/1985 | European Pat. Off. |
| 0170247 | 2/1986 | European Pat. Off. |
| 0 395 382 | 10/1990 | European Pat. Off. |
| 87/05300 | 9/1987 | WIPO |

OTHER PUBLICATIONS

Szebeni, Biochemistry 24, p. 2827, 1985.
Okamoto Takeshi, Liposome Containing Hemoglobin and Preparation Thereof, Jul. 11, 1990, Patent Abstracts of Japan–JP–A–02 178 233.
Abstraact, AN 92–118330, Derwent Publications Ltd., London, Feb. 26, 1992.
Abstract, AN 75–68422W, Derwent Publications Ltd., London, Mar. 24, 1975.
Beissinger et al, Liposome–encapsulated Hemoglobin as a Red Cell Surrogate–Preparation Scale–up, Jul.–Sep. 1986, 58–63.
Abstract, AN 89–117245, Derwent Publications Ltd., London, Mar. 8, 1989.
Abstract, AN 87–259765, Derwent Publications Ltd., London, Aug. 5, 1987.

*Primary Examiner*—Gollamudi S. Kishore
*Attorney, Agent, or Firm*—Burns, Doane, Swecker & Mathis, LLP

[57] ABSTRACT

A hemoglobin-encapsulating liposome having encapsulated thererin a hemoglobin solution having added thereto a substrate for an enzymatic reaction which produces reduced-form nicotinamide adenine dinucleotide (NADH) and/or reduced-form nicotinamide adenine dinucleotide phosphate (NADPH). Irreversible oxidation of hemoglobin with lapse of time is markedly suppressed.

7 Claims, 3 Drawing Sheets

Scheme of methemoglobin reduction mechanism in the hemoglobin-encapsulating liposome

HEMOGLOBIN-ENCAPSULATING LIPOSOME AND METHOD FOR MAKING THE SAME

This application is a continuation of application Ser. No. 08/214,133, filed Mar. 16, 1994 now abandoned.

BACKGROUND OF THE INVENTION

1. Industrial Utility Field

This invention is directed to a hemoglobin-encapsulating liposome adapted for administration into an organism. More particularly, this invention relates to a hemoglobin-encapsulating liposome wherein the hemoglobin encapsulated would undergo a minimized oxidation with lapse of time after administration into an organism.

2. Prior Art

Typical blood substitutes in current use include plasma expanders such as gelatin lysate solutions, dextran solutions, and hydroxyethyl starch (HES) solutions. Such blood substitutes, however, are preparations which have been developed in order to make up for the plasma in blood vessels and maintain blood circulation dynamics upon large-volume hemorrhage or other emergent occasions. Therefore, such blood substitutes are unable to substitute for oxygen-transportation capacity intrinsic to natural erythrocytes. Apart from such plasma expanders, development of artificial oxygen carriers is on its way for their use as blood substitutes provided with an oxygen-transportation capacity analogous to that of the natural erythrocytes.

At the initial stage of such development, chemically synthesized products making use of a fluorocarbon emulsion (perfluorochemical, PFC, often referred to as fluorocarbon) having a high oxygen-dissolving capacity (20 times that of water) were investigated. Such chemically synthesized products, however, have been found to have such defects as an insufficient oxygen-transportation capacity as well as accumulation in the organism.

On the other hand, attempts have been made to utilize hemoglobin from natural erythrocytes for the oxygen carrier. Use of such free hemoglobin under free conditions, however, is practically difficult since it suffers from an extremely short half time (not more than 4 hours) in the living body as well as low oxygen-transportation capacity to periphery and toxicity to kidney. Consequently, interests of the development have shifted to modified hemoglobins (stabilized hemoglobin, polymerized hemoglobin, etc.) and hemoglobins incorporated in liposomes, wherein the problems associated with the free hemoglobin have been obviated.

A typical hemoglobin-encapsulating liposome produced by thin film process is reported by Miller (U.S. Pat. No. 4,133,874). In this process, the hemoglobin-encapsulating liposomes are produced by dissolving a liposome-forming lipid in an adequate organic solvent such as chloroform, distilling off the organic solvent from the resulting solution to form a thin film of the lipid, adding a hemoglobin solution obtained by hemolysis onto the thus formed thin film, vigorously agitating the solution to form multilayer liposomes, and ultrasonically treating the thus formed multilayer liposomes. A merit of such process is relatively little denaturing of the hemoglobin due to reduced time of contact with oxygen.

It is reversible bonding of an oxygen molecule to the hemoglobin that is responsible for the oxygen-transportation capacity of the artificial erythrocytes prepared from hemoglobin, and such an oxygen-transportation capacity would be present only when the iron of hemoglobin (protoheme IX) is in its divalent ferrous state (i.e. $Fe^{2+}$). Hemoglobin, however, undergoes an oxidation in the course of its reversible oxygenation, and becomes to the trivalent ferric state ($Fe^{3+}$) called hemiglobin or methemoglobin which no longer has the power of transporting oxygen. Normal erythrocytes have a mechanism capable of suppressing such aforementioned hemoglobin oxidation. The hemoglobin solution prepared as an artificial oxygen carrier, however, does not have such oxidation suppression mechanism as found in natural erythrocytes. Consequently, proportion of the oxidized hemoglobin increases with lapse of time. In view of such a situation, upon use of the natural hemoglobin or its derivatives for a medical product or reagent, it has been necessary to add to the product or the reagent an antioxidant or a reducing agent such as sodium sulfite, sodium hydrogensulfite, ferrous sulfate, or sodium ethylenediaminetetraacetate, which would be toxic for an organism. It has also been usual to add reduced-form glutathione, ascorbic acid, a tocopherol, a sugar, an amino acid, or the like. These additives, however, have proved insufficient in suppressing the hemoglobin oxidation, and in particular, insufficient in suppressing the hemoglobin oxidation after the administration into an organism.

SUMMARY OF THE INVENTION

Figure 1:
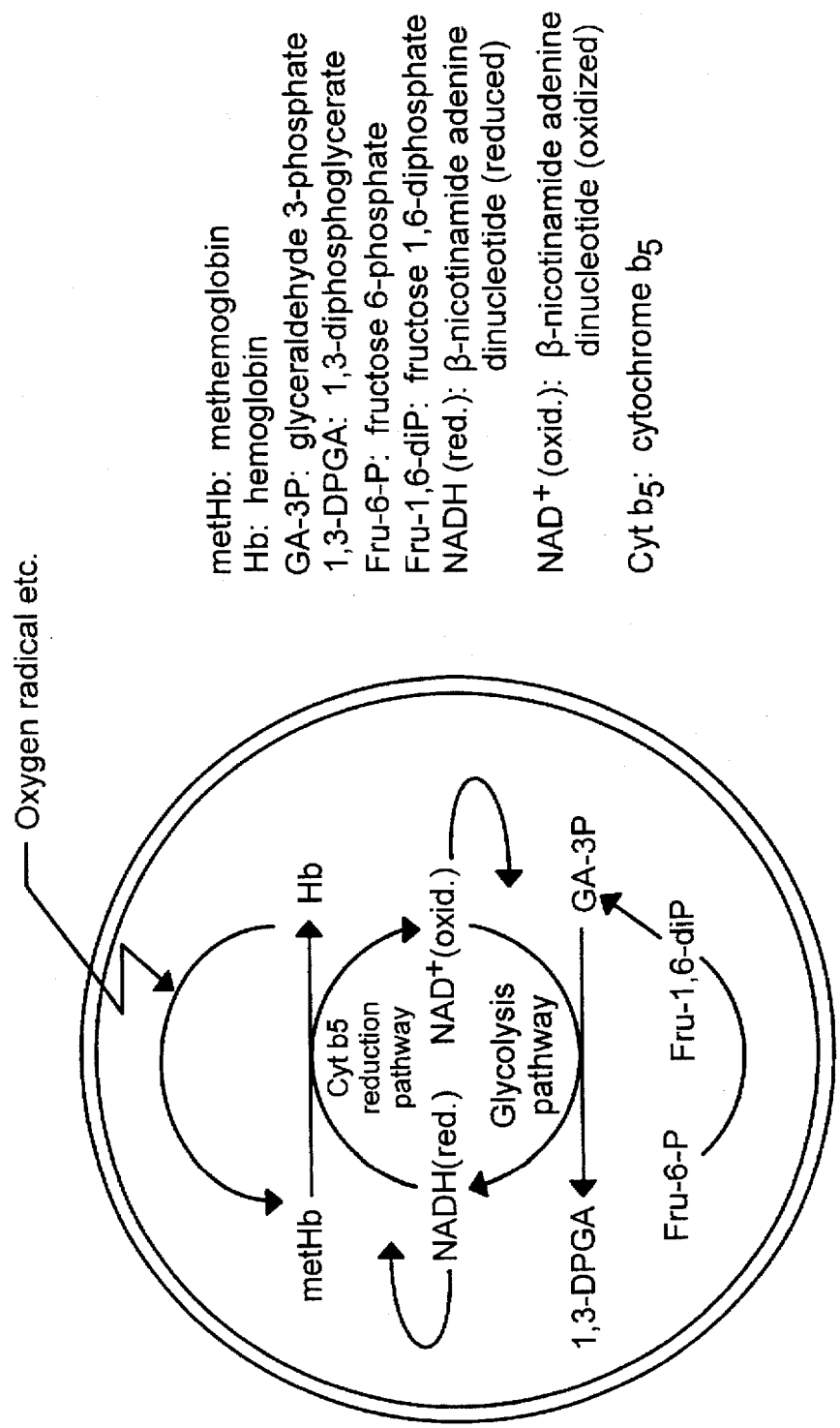
FIG. 1 is a schematic view showing oxidation/reduction cycle of the hemoglobin in a natural erythrocyte.

In view of the above-described situation, an object of the present invention is to provide a hemoglobin-encapsulating liposome wherein the hemoglobin oxidation with lapse of time, in particular, the hemoglobin oxidation after the administration into an organism is suppressed.

The problems as described above are obviated by the hemoglobin-encapsulating liposome being constructed as described below.

(1) A hemoglobin-encapsulating liposome comprising a liposome comprising a lipid; and a hemoglobin solution enclosed in said liposome, said hemoglobin solution having enzymatic activities inherited from natural erythrocyte and/or oxidation-reduction enzyme activities, and has added thereto a substrate for an enzymatic reaction which produces reduced-form nicotinamide adenine dinucleotide (NADH) and/or reduced-form nicotinamide adenine dinucleotide phosphate (NADPH).

The substrate for such an enzymatic reaction may preferably be added in an amount of from 0.1 to 25 mole per 1 mole of the hemoglobin.

(2) The hemoglobin-encapsulating liposome according to (1) wherein the substrate for such enzymatic reaction which produces reduced-form nicotinamide adenine dinucleotide (NADH) and/or reduced-form nicotinamide adenine dinucleotide phosphate (NADPH) is an organic acid or a derivative thereof.

(3) The hemoglobin-encapsulating liposome according to (1) or (2) wherein the organic acid or a derivative thereof is at least one member selected from the group consisting of malic acid, oxaloacetic acid, citric acid, isocitric acid, α-ketoglutaric acid, succinyl-CoA (succinyl derivative of coenzyme A), succinic acid, fumaric acid, aspartic acid, pyruvic acid, phosphoenolpyruvic acid, acetyl-CoA (acetyl derivative of coenzyme A), and glutamic acid.

(4) The hemoglobin-encapsulating liposome according to (1) wherein the substrate for such enzymatic reaction which produces reduced-form nicotinamide adenine dinucleotide (NADH) and/or reduced-form nicotinamide adenine dinucleotide phosphate (NADPH) is a sugar metabolic intermediate in anaerobic glycolysis.

(5) The hemoglobin-encapsulating liposome according to (4) wherein the sugar metabolic intermediate in anaerobic glycolysis is at least one member selected from glucose, glucose 6-phosphate, glucose 1,6-diphosphate, fructose 6-phosphate, UDP-glucose, L-glonate, xylitol, sorbitol, α-glycerol phosphate, glyceraldehyde 3-phosphate, and lactate.

(6) The hemoglobin-encapsulating liposome according to any one of (1) to (5) wherein the hemoglobin solution further comprises an organophosphate compound.

The organophosphate compound may preferably be added in an amount of from 0.05 to 4 mole per 1 mole of the hemoglobin.

The organophosphate compound may preferably be inositol hexaphosphate.

(7) The hemoglobin-encapsulating liposome according to any one of (1) to (6) wherein the lipid has added thereto a tocopherole analogue or a derivative thereof.

The tocopherole analogue or a derivative thereof may preferably be added in an amount of from 0.5 to 4.5 mole % of the total lipid content of the liposome membrane.

(8) The hemoglobin-encapsulating liposome according to any one of (1) to (7) wherein said hemoglobin solution has further added thereto at least one enzyme selected from the group consisting of reduced-form nicotinamide adenine dinucleotide (NADH), oxidized-form nicotinamide adenine dinucleotide (NAD), reduced-form nicotinamide adenine dinucleotide phosphate (NADPH), and oxidized-form nicotinamide adenine dinucleotide phosphate (NADP$^+$).

The enzyme may preferably be added in an amount of from 0.1 to 25 mole per 1 mole of the hemoglobin.

(9) A method for preparing a hemoglobin-encapsulating liposome according to any one of (1) to (8) comprising the steps of (a) preparing a concentrated hemoglobin solution having a hemoglobin concentration of 30 to 60% by weight by subjecting rinsed erythrocytes to hemolysis, removing stroma component, and concentrating the stroma-free hemoglobin solution;

(b) adding to the concentrated hemoglobin solution a substrate for an enzymatic reaction which produces at least one member selected from the group consisting of reduced-form nicotinamide adenine dinucleotide (NADH) and reduced-form nicotinamide adenine dinucleotide phosphate (NADPH) and stirring the resulting hemoglobin solution; and (c) liposomerizing the hemoglobin solution under moderate conditions to prevent enzymes in the hemoglobin solution from losing their activities.

The liposomerization may preferably be conducted under moderate conditions of injecting the hemoglobin solution for one to several times from an orifice at a temperature of up to 40° C. and at a pressure in the range of from 50 to 1,800 kg/cm$^2$.

DETAILED DESCRIPTION OF THE INVENTION

In the present invention, loss of the oxygen transportation capacity of the hemoglobin-encapsulating liposome due to hemoglobin oxidation with lapse of time is prevented by adding to the hemoglobin solution a substrate for an enzymatic reaction which produces reduced-form nicotinamide adenine dinucleotide (NADH) and/or reduced-form nicotinamide adenine dinucleotide phosphate (NADPH) to thereby reduce the oxidized hemoglobin which has generated with lapse of time.

The substrate for an enzymatic reaction which would produce reduced-form nicotinamide adenine dinucleotide (NADH) and/or reduced-form nicotinamide adenine dinucleotide phosphate (NADPH) which may be used in the present invention is not limited to any particular type, so long as it produces NADH or NADPH as a result of at least one enzymatic reaction promoted by a single enzyme or by a combination of enzymes present in the organism. Preferred substrate is an organic acid or a derivative thereof, and the most preferred is malic acid since it would produce NADH by a single enzymatic reaction. Other organic acids that would produce malic acid through citric acid cycle (tricarboxylic acid (TCA) cycle, Krebs cycle) may also be utilized, for example, oxaloacetic acid, citric acid, isocitric acid, α-ketoglutaric acid, succinyl-CoA, succinic acid, fumaric acid, aspartic acid, pyruvic acid, phosphoenolpyruvic acid, ethanolpyruvic phosphate, acetyl-CoA, and glutamic acid. Other compounds that may be used for the substrate are sugar metabolic intermediates in anaerobic glycolysis, for example, glucose, glucose 6-phosphate, glucose 1,6-diphosphate, fructose 6-phosphate, UDP-glucose, L-glonate, xylitol, sorbitol, α-glycerol phosphate, glyceraldehyde 3-phosphate, and lactate. Namely, any composition that produces NADH and/or NADPH as a result of an enzymatic reaction promoted by a single enzyme or by a combination of enzymes present in the organism may be used as the substrate. It should be noted that use of substrates in combination of two or more would also be adequate in some cases.

In the present invention, the substrate for an enzymatic reaction that would produce NADH and/or NADPH may be added in an amount of from 0.1 to 25 mole, preferably in an amount of from 1 to 20 mole, and more preferably in an amount of from 4 to 12 mole per 1 mole of the hemoglobin. An addition of the substrate in an amount of less than 0.1 mole per 1 mole of the hemoglobin is insufficient to prevent the formation of the methemoglobin. An addition of the substrate in an amount of more than 25 mole per 1 mole of the hemoglobin would alter the flowability of the hemoglobin solution to result in a reduced amount of the hemoglobin solution encapsulated in the liposome, and hence, in a reduced liposomerization efficiency.

The lipid used for the formation of the liposome is not limited to any particular type so long as it is capable of forming the liposome, and both natural and synthetic lipids may be used for such a purpose. Exemplary lipids include lecithin (phosphatidylcholine), phosphatidylethanolamine, phosphatidic acid, phosphatidylserine, phosphatidylinositol, phosphatidylglycerol, sphingomyelin, cardiolipin, and hydrogenated derivatives thereof, which may be used either alone or in combination of two or more.

In preparing the hemoglobin solution used in the present invention, erythrocytes are first hemolyzed in a buffer in accordance with normal process, and stroma (erythrocyte membrane) is removed therefrom. The resulting stroma-free aqueous hemoglobin solution is then concentrated by ultrafiltration using a membrane adapted for fractionation of molecules having a molecular weight of 10,000 to a concentration of at least 30% (w/v), preferably, to a concentration of from 30 to 60% (w/v), and more preferably, to a concentration of from 40 to 50% (w/v). The hemoglobin solution is concentrated to such a range in order to maximize the amount of the hemoglobin enclosed in the liposome within liposomerizable concentration range since the amount of oxygen transported to periphery would increase with an increase in the amount of hemoglobin enclosed in the liposome.

In the present invention, it is also preferred to add to the hemoglobin solution an organic phosphate compound such as inositol hexaphosphate, tetrapolyphosphate, pyridoxal 5'-phosphate, or ATP to adjust the amount of oxygen released in periphery. Preferably, the phosphate compound is added to the hemoglobin solution in an amount of from 0.5 mole to 1.5 mole per 1 mole of the hemoglobin. The amount added may differ in accordance with the type of the compound employed.

The erythrocytes used in the present invention are not limited to any particular type so long as they are, when the hemoglobin-encapsulating liposome of the present invention is administered to human, of human origin. Although use of fresh erythrocytes is preferred, erythrocytes that had been stored for more than 50 days at 4° C. are still adequate for use.

In addition to the substrate for enzymatic reaction, the hemoglobin solution of the present invention may have further added thereto at least one enzyme selected from the group consisting of reduced-form nicotinamide adenine dinucleotide (NADH), oxidized-form nicotinamide adenine dinucleotide (NAD), reduced-form nicotinamide adenine dinucleotide phosphate (NADPH), and oxidized-form nicotinamide adenine dinucleotide phosphate (NADP). The enzyme may be added in an amount of from 0.1 to 25 mole per 1 mole of the hemoglobin.

The liposome of the present invention may have added thereto a tocopherol analogue, namely, vitamin E in order to prevent oxidation. Tocopherol has four isomers, $\alpha$, $\beta$, $\gamma$, and $\delta$, and any of such isomers may be used in the present invention. The tocopherol may be added in an amount of from 0.5 to 4.5% by mole, and preferably, from 1.0 to 2.0% by mole per total amount of the lipid.

In the present invention, a charge donor, for example, a sterol or a fatty acid may be added as a component of the liposome membrane to strengthen the film structure and to adjust the period of digestion after its administration.

The hemoglobin-encapsulating liposome of the present invention may be produced by subjecting rinsed erythrocytes to hemolysis, removing stroma (erythrocyte membrane) component, concentrating the hemoglobin solution to a concentration of 30 to 60% (w/v); adding malic acid to the concentrated hemoglobin solution and agitating the mixed solution, and liposomerizing the solution under moderate conditions to prevent the enzymes in the hemoglobin solution from losing their enzymatic activity. The moderate conditions for preventing loss of enzymatic activity include an injection from an orifice for once to several times at a high pressure of from 50 to 1,800 kg/cm$^2$, and preferably, from 80 to 1,200 kg/cm$^2$. The liposomerization should be carried out at a temperature of up to 40° C. The temperature is maintained during the liposomerization at 40° C. or less preferably at 0° C. For example, the liposomerization may be carried out at a pressure of from 480 to 1,450 kg/cm$^2$ when the high-pressure injection emulsifier used is Microfluidizer 110Y (Microfluidizer Co.), or at a pressure of from 80 to 200 kg/cm$^2$ when Parr cell disruptor (Parr Co.) is used. It should be noted that, in either case, the liposomerization is to be carried out at a temperature of up to 40° C., and preferably, at a temperature of up to 4° C., more preferably at 0° C.

In natural erythrocytes, hemoglobin undergoes a reversible hemoglobin-methemoglobin reaction. More illustratively, the hemoglobin is oxidized into methemoglobin with lapse of time, but at the same time, the methemoglobin is reduced to hemoglobin by the action of enzymes in the erythrocytes, as shown in FIG. 1. However, once the hemoglobin is taken out of the natural erythrocyte as in the case of the present invention to be encapsulated into a liposome, the methemoglobin reduction mechanism is no longer active, and the hemoglobin which had been once converted into methemoglobin would never be reduced. The oxygen-transportation capacity is thereby lost. Under the hypothesis that such loss of the methemoglobin reduction mechanism is caused by the loss of enzymatic activities due to excessive physical energy or heat applied during the liposomerization, liposomerization conditions were examined and hemoglobin-encapsulating liposomes were produced under more moderate conditions to maintain the enzymatic activity of the hemoglobin solution. More illustratively, hemoglobin-encapsulating liposomes were produced by injecting the solution through an orifice for once to several times at a pressure of from 50 to 1,600 kg/cm$^2$, and more preferably from 80 to 1,200 kg/cm$^2$. However, upon administration of the thus produced hemoglobin-encapsulating liposome, the hemoglobin still underwent oxidation.

The inventors of the present invention have made a further intensive study and found out that, such hemoglobin oxidation with lapse of time after administration into an organism can be significantly suppressed by producing the hemoglobin-encapsulating liposomes under moderate conditions as described above, and adding to the hemoglobin solution a substrate for an enzymatic reaction which would produce NADH and/or NADPH.

Figure 2:
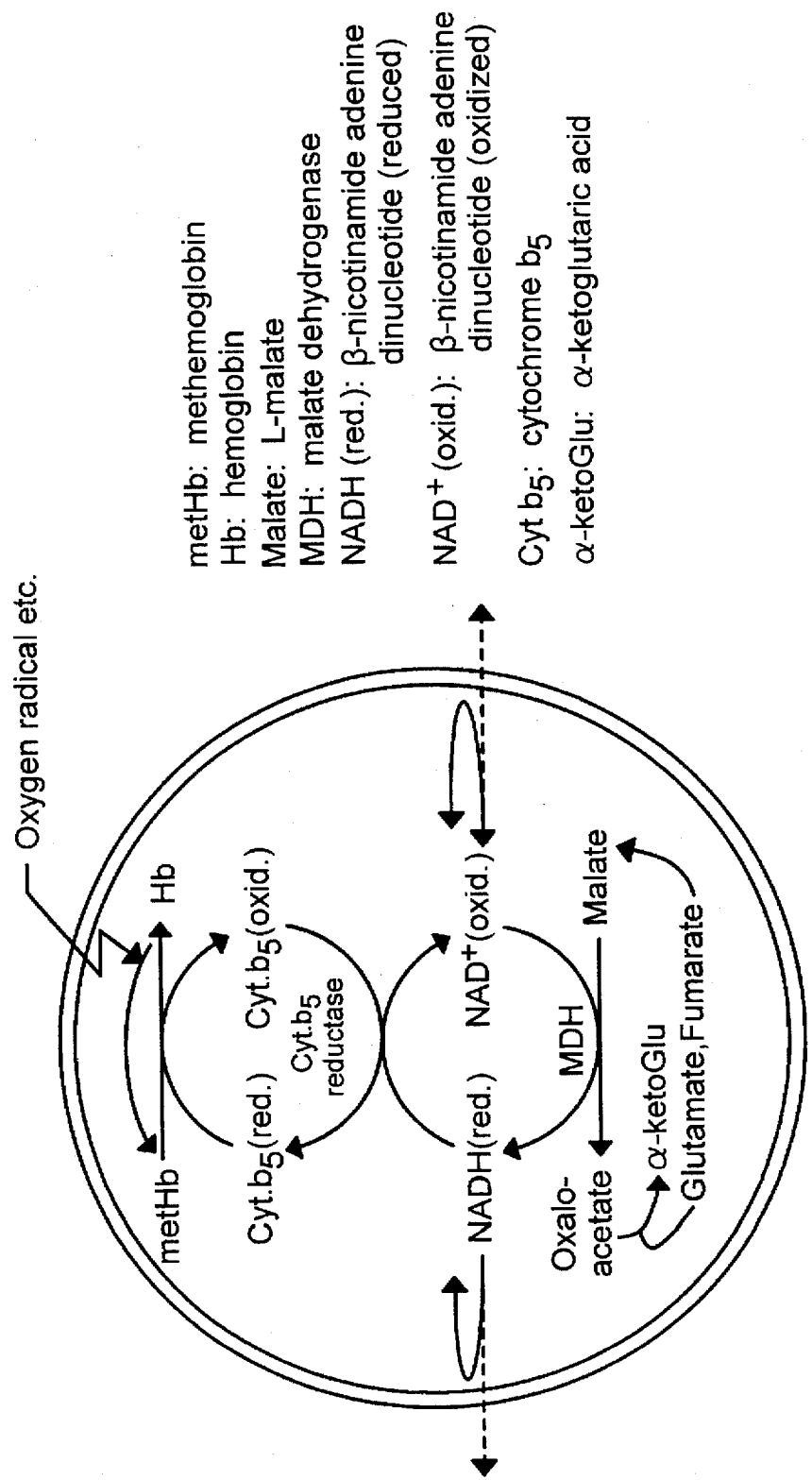
FIG. 2 is a schematic view showing oxidation/reduction cycle of the hemoglobin in the hemoglobin-encapsulating liposome of the present invention.

It has been deduced that the mechanism for such suppression of the hemoglobin oxidation is as described below, where the explanation is made by taking an example of malic acid. When the liposomerization is carried out under moderate conditions as described above, the enzymes in the hemoglobin solution would not undergo a loss in their enzymatic activities. However, in the stages of the hemoglobin isolation by removing membrane components from natural erythrocytes, or purification and concentration of the thus isolated hemoglobin, substances required for the subsequent enzymatic reactions such as substrates for enzymatic reactions or coenzymes having a molecular weight of up to 10,000 would be lost to subsequently result in the absence of the methemoglobin-reduction enzymatic reaction. When malic acid is added to the hemoglobin solution, malic acid would serve a substrate for the enzymatic reaction regenerating NADH required for the methemoglobin-reduction reaction. More illustratively, NADH would be regenerated simultaneously with the conversion of the malic acid into oxaloacetic acid by malic acid dehydrogenase to thereby induce the methemoglobin reduction reaction equivalent to the one in natural erythrocytes, as shown in FIG. 2. It is deduced that the hemoglobin oxidation with lapse of time is thereby suppressed.

Natural mature erythrocytes are free from nucleus and organelle such as mitochondria or ribosome, and consequently, incapable of synthesizing any protein or lipid. Since the mature erythrocytes are free from mitochondria, it does not have TCA cycle (citric acid cycle), and ATP (adenosine triphosphate) necessary for maintaining its shape and function is mainly produced through Embden-Meyerhof pathway (EMP, anaerobic glycolysis pathway). Under physiological conditions, glucose is phosphorylated with hexokinase to glucose 6-phosphate, and under normal conditions, 90% of the glucose is metabolized through Embden-Meyerhof pathway, and the remaining 5 to 10% of the glucose is metabolized through hexose monophosphate shunt (HMS or HMP).

However, as will be demonstrated in the Examples, the inventors of the present invention have confirmed that, some enzymes involved in TCA cycle are present in the stroma-free hemoglobin solution prepared in the present invention with their enzymatic activities preserved, although such enzymes are not generally expected to be present in such stroma-free hemoglobin solution.

In other words, the inventors of the present invention have made an effective use of such residual enzymatic activity inherited from natural erythrocytes, and replenished the hemoglobin solution with necessary substrates optionally with enzymes to prepare a liposome-type artificial oxygen transportor, namely, the hemoglobin-encapsulating liposome, having an enzymatic methemoglobin reduction mechanism analogous to the natural erythrocytes.

The present invention is described in further detail by referring to the following Examples.

EXAMPLES

It should be noted that, unless otherwise noted, various stages of the preparation were aseptically carried out under the cooled conditions of 4° C. The reagents and instruments used had been sterilized, and an aseptic ultra-pure water (at least 15 megΩ.C.cm at 25° C., pyrogen-free) containing no residual heavy metal ions or inorganic ions was used for the preparation.

Example 1

(1) Preparation of concentrated stroma-free hemoglobin (SFH) solution 15 liters (200 ml×75 bags) of thickened erythrocytes were rinsed with physiological saline using continuous flow centrifuge to remove platelets, leucocytes and other plasma components that had been contained with the erythrocytes to obtain roughly rinsed erythrocytes. The roughly rinsed erythrocytes were further rinsed with physiological saline using a filter having a pore size of 0.45 µm, and to 5 liters of the thus rinsed erythrocytes was added 10 liters of hypotonic phosphate buffer solution (10 mM, pH 7.4) for hemolysis. The resulting product was applied to a plasma separator having a pore size of 0.45 µm to remove erythrocyte membrane (stroma) and filtered through a filter having a pore size of 0.1 µm for bacterial filtration to recover about 12 liters of stroma-free hemoglobin (SFH) solution having a hemoglobin concentration of 8% (w/v). The resulting solution was dialyzed with a hollow fiber-type dializer (TAF-10SS, Terumo Corporation) against 10 mM 2-[4-(2-hydroxyethyl-piperazynyl)]ethanesulfonic acid (HEPES) buffer (pH 7.4), and then concentrated by ultrafiltration to obtain about 1.8 liters of SFH solution having a hemoglobin concentration of 50% (w/v).

(2) Addition of reagents to the concentrated SFH solution

To 4 ml of HEPES buffer solution (50 mM, pH 7.4) were added monosodium malate (L-malic acid, monosodium salt, SIGMA Chem. Co.) in a molar amount 4 times the molar amount of the hemoglobin in 100 ml of the concentrated SFH solution prepared in the above-described step (1) and sodium phytate (inositol hexaphosphoric acid dodecasodium salt, SIGMA Chem. Co.) in a molar amount 0.8 times the molar amount of the hemoglobin in the concentrated SFH solution. The resulting solution was added to 100 ml of the concentrated SFH solution, and the resulting mixture was stirred until the added reagents were homogeneously incorporated in the hemoglobin solution.

(3) Liposomerization of the reagent-mixed solution

To 18 grams of a uniformly mixed powder (Presome, Nippon Seika) comprising purified satisfied phosphatydylchorine (HSPC) having a hydrogenation rate of 90%, cholesterol (Chol), myristic acid (MA) and tocopherol (TOC) in a HSPC:Chol:MA:TOC molar ratio of 7:7:2:0.28 was added an equal amount of aseptic purified water, and the mixture was heated to a temperature of from 60° to 70° C. to allow for swelling. To the thus swelled starting lipid material was added 100 ml of the reagent-mixed solution prepared in the above Example 1(2) and the mixture was agitated for 30 seconds. The thus prepared lipid-concentrated SFH mixed solution was fed to Microfluidizer 110Y (Microfluidics Co.) wherein liposomerization was conducted in ice bath and at a pressure of 12,000 psi (about 844 kg/cm$^2$).

(4) Purification of the hemoglobin-encapsulating liposome

The product of Example 1(3) was diluted with and suspended in an equal amount of physiological saline and dextran 40 injection, and the resulting suspension was subjected to centrifugation at 10,000 rpm (13,000 g) for 30 minutes at 4° C. The liposomes having the hemoglobin solution encapsulated therein at a high efficiency were collected as the centrifugate. The supernatant containing the residual free hemoglobin which failed to be liposomerized as well as the starting lipid components was removed by decantation or suction. The above-described washing process was repeated until no free hemoglobin was recognized in the supernatant with naked eye. The resulting product was filtered through Durapore (polyvinylidene difluoride) membrane filter (Minitan System, a plasma separator manufactured by Millipore Ltd.) having a pore size of 0.45 µm to remove coarse particles in the suspension. The filtrate was finally concentrated with a hollow fiber-type dializer (TAF-10SS, Terumo K.K.), and the concentrate was adjusted with physiological saline to a hemoglobin concentration of 10% (w/v) to produce about 80 ml of purified hemoglobin-encapsulating liposome suspension.

Example 2

(1) Preparation of concentrated SFH solution

The procedure of Example 1(1) was repeated to produce a concentrated SFH solution.

(2) Addition of reagents to the concentrated SFH solution

To 8 ml of HEPES buffer solution (50 mM, pH 7.4) were added monosodium malate (L-malic acid, monosodium salt, SIGMA Chem. Co.) in a molar amount 2 times the molar amount of the hemoglobin in 100 ml of the concentrated SFH solution prepared in the above-described step (1), sodium phytate (inositol hexaphosphoric acid dodecasodium salt, SIGMA Chem. Co.) in a molar amount 0.8 times the molar amount of the hemoglobin, and oxidized-form β-NAD$^+$ (BMY., Grade II, 98%) in a molar amount 0.2 times the molar amount of the hemoglobin. The resulting solution was added to 100 ml of the concentrated SFH solution, and the resulting mixture was stirred until the added reagents were homogeneously incorporated in the hemoglobin solution.

(3) Liposomerization of the reagent-mixed solution

To 18 grams of a uniformly mixed powder (Presome, Nippon Seika) comprising purified satisfied phosphatydylchorine (HSPC) having a hydrogenation rate of 90%, cholesterol (Chol), myristic acid (MA) and tocopherol (TOC) in a HSPC:Chol:MA:TOC molar ratio of 7:7:2:0.28 was added an equal amount of aseptic purified water, and the mixture was heated to a temperature of from 60° to 70° C. to allow for swelling. To the thus swelled starting lipid material was added 100 ml of the reagent-mixed solution prepared in the above Example 2(2) and the mixture was agitated for 30 seconds. The thus prepared lipid-concentrated SFH mixed solution was fed to Microfluidizer 110Y (Microfluidics Co.) wherein liposomerization was conducted in ice bath and at a pressure of 12,000 psi (about 844 kg/cm$^2$).

(4) Purification of the hemoglobin-encapsulating liposome

The product of Example 2(3) was diluted with and suspended in an equal amount of physiological saline and dextran 40 injection, and the resulting suspension was subjected to centrifugation at 10,000 rpm (13,000 g) for 30 minutes at 4° C. The liposomes having encapsulated therein the hemoglobin at a high efficiency were collected as centrifugate. The supernatant containing the residual free hemoglobin which failed to be liposomerized as well as the starting lipid components was removed by decantation or suction. The above-described washing process was repeated until no free hemoglobin was recognized in the supernatant with naked eye. The resulting product was filtered through Durapore (polyvinylidene difluoride) membrane filter (Minitan System, Millipore Ltd.) having a pore size of 0.45 μm to remove coarse particles in the suspension. The filtrate was finally concentrated with a hollow fiber-type dializer (TAF-10SS, Terumo K.K.), and the concentrate was adjusted with physiological saline to a hemoglobin concentration of 10% (w/v) to produce about 80 ml of purified hemoglobin-encapsulating liposome suspension.

Example 3

(1) Preparation of concentrated SFH solution

The procedure of Example 1(1) was repeated to produce a concentrated SFH solution.

(2) Addition of reagents to the concentrated SFH solution

To 10 ml of HEPES buffer solution (50 mM, pH 7.4) were added monosodium malate (L-malic acid, monosodium salt, SIGMA Chem. Co.) in a molar amount 4 times the molar amount of the hemoglobin in 100 ml of the concentrated SFH solution prepared in the above-described step (1), sodium phytate (inositol hexaphosphoric acid dodecasodium salt, SIGMA Chem. Co.) in a molar amount 1.0 times the molar amount of the hemoglobin, β-NADPH.Na$_4$ (Kyowa Hakko Kogyo Co. Ltd.) in a molar amount 1.0 times the molar amount of the hemoglobin, and sodium glucose 6-phosphate (Sigma Chem. Co.) in an amount equivalent to 5 mM. The resulting solution was added to the concentrated SFH solution, and the resulting mixture was stirred until the added reagents were homogeneously incorporated in the hemoglobin solution.

(3) Liposomerization of the reagent-mixed solution

To 18 grams of a uniformly mixed powder (Presome, Nippon Seika) comprising purified satisfied phosphatydylchorine (HSPC) having a hydrogenation rate of 90%, cholesterol (Chol), myristic acid (MA) and tocopherol (TOC) in a HSPC:Chol:MA:TOC molar ratio of 7:7:2:0.28 was added an equal amount of aseptic purified water, and the mixture was heated to a temperature of from 60° to 70° C. to allow for swelling. To the thus swelled starting lipid material was added 100 ml of the reagent-mixed solution prepared in the above Example 3(2) and the mixture was agitated for 30 seconds. The thus prepared lipid-concentrated SFH mixed solution was fed to Parr cell disruptor (Parr Co.) and helium gas was pressurized to 100 kg/cm$^2$, which pressure was kept for 30 minutes. Liposomerization was carried out by injecting the mixed solution from the Parr cell disruptor through its orifice nozzle in ice bath while the pressure was maintained at the same level.

(4) Purification of the hemoglobin-encapsulating liposome

The product of Example 3(3) was diluted with and suspended in an equal amount of physiological saline and dextran 40 injection, and the resulting suspension was subjected to centrifugation at 10,000 rpm (13,000 g) for 30 minutes at 4° C. The liposomes having encapsulated therein the hemoglobin at a high efficiency were collected as centrifugate. The supernatant containing the residual free hemoglobin which failed to be liposomerized as well as the starting lipid components was removed by decantation or suction. The above-described washing process was repeated until no free hemoglobin was recognized in the supernatant with naked eye. The resulting product was filtered through Durapore (polyvinylidene difluoride) membrane filter (Minitan System, Millipore Ltd.) having a pore size of 0.45 μm to remove coarse particles in the suspension. The filtrate was finally concentrated with a hollow fiber-type dializer (TAF-10SS, Terumo K.K.), and the concentrate was adjusted with physiological saline to a hemoglobin concentration of 10% (w/v) to produce about 80 ml of purified hemoglobin-encapsulating liposome suspension.

Comparative Example 1

Hemoglobin-encapsulating liposomes were prepared by repeating the procedure of Example 1 except that the hemoglobin solution did not have the sodium L-malate added thereto, and the liposomerization was carried out using a Waring blender under the conditions as described below.

Liposomerization conditions using the Waring blender

Warling blender: Warling Co. Blender 7010S

Volume of the SFH mixed solution: 200 ml

Amount of the lipid: 36 g (swelled with an equal amount of aseptic purified water)

Rotation rate: 15,000 rpm

Time of treatment: 30 minutes

A cycle of (1) treatment for 3 minutes and (2) cooling at 4° C. for 10 minutes was repeated.

Figure 3:
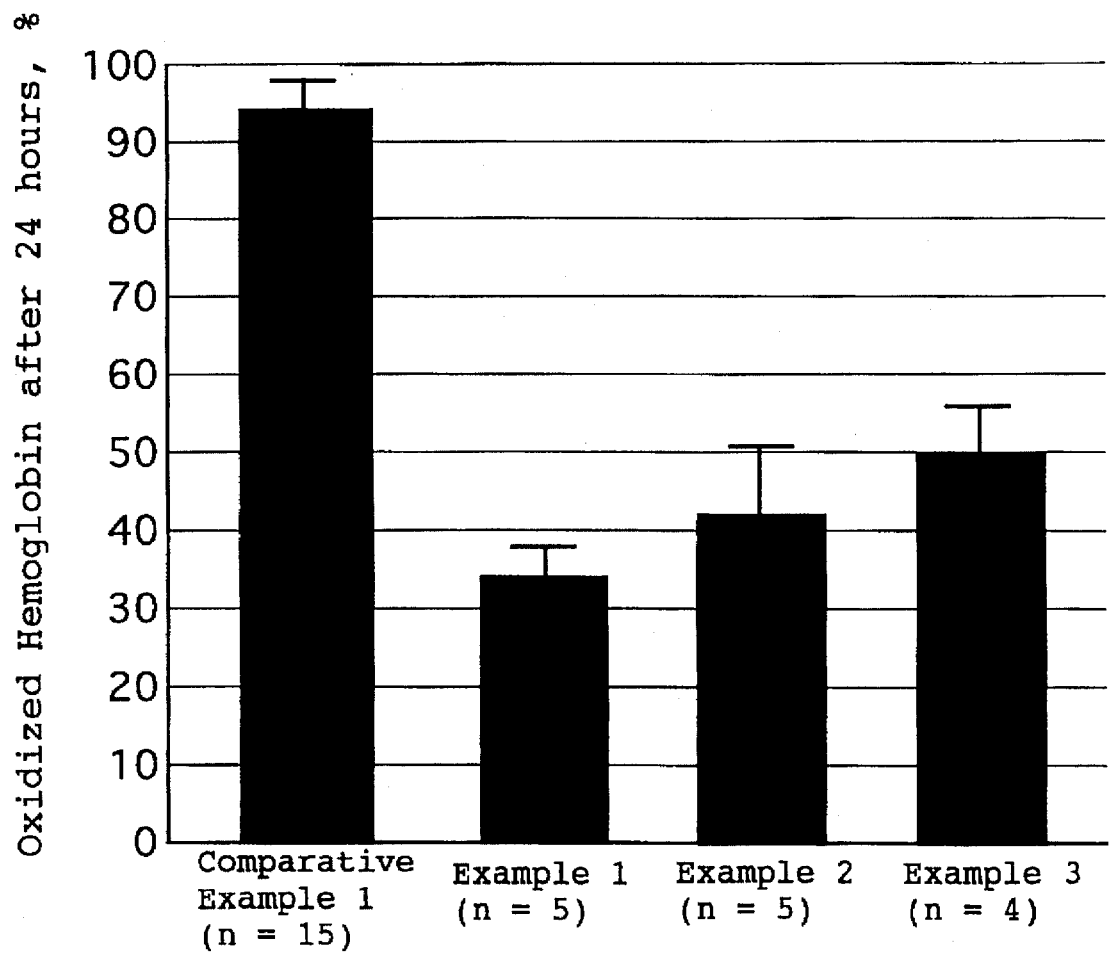
FIG. 3 illustrates effects of methemoglobin reduction of the hemoglobin-encapsulating liposomes of the present invention and the Comparative Example.

The hemoglobin-encapsulating liposomes prepared in Examples 1 to 3 and Comparative Example 1 were evaluated by the procedure as described below. The results are shown in Table 1 and FIG. 3.

Measurement of hemoglobin oxidation after 24 hours (in vivo)

The thus prepared suspensions of the hemoglobin-encapsulating liposomes were adjusted to a hemoglobin content of 5% (w/v). To a male ICR mouse of 5 week old was administered 1 ml of the liposome suspension from its tail vein. After 24 hours, whole blood was collected from its abdominal large vein, and oxidation rate was calculated by the procedure as described below.

The hemoglobin-encapsulating liposomes are more resistant to a change in osmotic pressure compared to the natural erythrocytes, and separation of the hemoglobin-encapsulating liposomes from the natural erythrocytes was carried out by utilizing such a property. More illustratively, the collected whole blood having added heparin thereto was mixed with 8 to 10 volumes of ultra-pure water to allow for the natural mouse erythrocytes to undergo hemolysis. The mixture was then subjected to a high-speed centrifugation at 18,000 rpm for 30 minutes at 4° C. to collect the hemoglobin-encapsulating liposomes as the centrifugate. The above-described procedure was repeated for 3 times to completely remove the blood components from the sample. To the thus obtained sample was added 2.0 ml of 10% (w/v) Triton X100-HEPES buffer (0.5M, pH 7.4), and the mixture was vigorously agitated for about 1 minute. To the mixture was also added 2 ml of Freon, and the mixture was agitated for another about 1 minute. The resulting solution was centrifuged at 3,000 rpm for 15 minutes, and 1 ml of HEPES buffer was added to about 1.8 ml of the supernatant. The resulting product was evaluated for its absorption spectrum in the visible range (460 nm to 700 nm) to calculate the rate of oxidation with lapse of time.

The concentration for each of oxyhemoglobin, methemoglobin and hemichrome was calculated by multi-wave length spectroscopy (700 nm, 630 nm, 577 nm and 560 nm) in accordance with the preliminarily measured values in the hemoglobin absorption curve (as indicated below).

oxyHb (µM)=29.8×ΔAbs (577 nm)−9.8×ΔAbs (630 nm)−22.2×ΔAbs (560 nm)

metHb (µM)=7×ΔAbs (577 nm)+76.8×ΔAbs (630 nm)−13.8×ΔAbs (560 nm)

hemichrome (µM)=−33.2×ΔAbs (577 nm)−36×ΔAbs (630 nm)+58.2×ΔAbs (560 nm), with the proviso ΔAbs (577 nm)=Abs (577 nm)−Abs (700 nm)
ΔAbs (630 nm)=Abs (630 nm)−Abs (700 nm)
ΔAbs (560 nm)=Abs (560 nm)−Abs (700 nm).

TABLE 1

| Sample | Initial metHb % | Increase in 24 hr, in vivo, % | | Total oxidized Hb* |
|---|---|---|---|---|
| | | metHb | Hemichrome | |
| Comparative Example 1 (n = 15) Mean | 11.60 ± 4.49 | 49.49 ± 10.38 | 32.52 ± 9.24 | 93.61 ± 3.46 |
| Example 1 (n = 5) Mean | 3.06 | 23.03 ± 2.42 | 7.41 ± 1.99 | 33.50 ± 4.31 |
| Example 2 (n = 5) Mean | 2.42 | 24.63 ± 1.45 | 15.05 ± 7.82 | 42.09 ± 9.12 |
| Example 3 (n = 5) Mean | 2.97 | 28.57 ± 2.60 | 19.31 ± 3.72 | 50.86 ± 5.39 |

Hb: hemoglobin;
S.D.: standard deviation;
*methemoglobin + hemichrome.

As apparent from the results of Table 1, oxidation of the hemoglobin after a predetermined period of the hemoglobin-encapsulating liposomes obtained in Examples 1, 2 and 3 according to the present invention is significantly reduced as compared to that of the hemoglobin-encapsulating liposomes obtained in Comparative Example 1.

Example 4

(1) Preparation of methemoglobin-rich concentrated SFH solution

The concentrated SFH solution prepared in Example 1(1) was incubated at 37° C. for 4 days to prepare a concentrated SFH solution having a methemoglobin content of 35%. To the thus prepared methemoglobin-rich solution was added a fresh concentrated SFH solution having a methemoglobin content of not more than 2% to prepare a methemoglobin-rich concentrated SFH solution having a methemoglobin content of 17%.

(2) Addition of reagents to the methemoglobin-rich concentrated SFH solution

To 8 ml of HEPES buffer solution (50 mM, pH 7.4) were added monosodium malate (L-malic acid, monosodium salt, SIGMA Chem. Co.) in a molar amount 4 times the molar amount of the hemoglobin in 100 ml of the concentrated SFH solution prepared in the above-described step (1), sodium phytate (inositol hexaphosphoric acid dodecasodium salt, SIGMA Chem. Co.) in a molar amount 0.8 times the molar amount of the hemoglobin, oxidized-form β-NAD⁺ (β-nicotin-amide adenine dinucleotide disodium salt, oxidized, BMY., Grade II, 98%) in a molar amount 0.2 times the molar amount of the hemoglobin, and reduced-form β-NADH (β-nicotinamide adenine dinucleotide disodium salt, reduced, BMY, Grade II, 98%) in a molar amount 0.2 times the molar amount of the hemoglobin. The resulting solution was added to 100 ml of the methemoglobin-rich concentrated solution, and the resulting mixture was stirred until the added reagents were homogeneously incorporated in the hemoglobin solution.

(3) Liposomerization of the reagent-mixed solution

The thus prepared mixed solution was liposomerized by repeating the procedure of Example 1(3).

(4) Purification of the hemoglobin-encapsulating liposome

The thus prepared liposomes were purified by repeating the procedure of Example 1(4).

Comparative Example 2

The procedure of Example 4 was repeated except that the sodium phytate of equal amount was the only reagent added to the HEPES buffer in step (2).

Hemoglobin oxidation immediately after preparation

The hemoglobin-encapsulating liposomes prepared in Example 4 and Comparative Example 3 were evaluated for their hemoglobin oxidation immediately after their preparation by measuring their absorption spectrum by the multi-wave length spectroscopy to calculate the degree of oxidation. The results are shown in Table 2.

TABLE 2

| Sample | Hemoglobin OxyHb | Oxidized hemoglobin | |
|---|---|---|---|
| | | metHb | Hemichrome |
| Comparative Example 2 (control, having no malate, NAD⁺ or NADH added) | 84.0% | 10.8% | 5.2% |
| Example 4 (having malate, NAD⁺ and NADH added) | 96.3% | 1.5% | 2.2% |

Hb: hemoglobin;

The results shown in Table 2 reveal that, in the case of the hemoglobin-encapsulating liposomes of Example 4 having malate, NAD$^+$ and NADH added thereto before the liposomerization, concentration of the oxidized hemoglobin underwent a significant decrease in the course of their preparation.

Experiments

The lipid-SFH mixed solution prepared in Example 1(3) was evaluated for its NADH-methemoglobin reductase activity and malate dehydrogenase activity before and after the liposomerization with the Microfluidizer by the procedure as described below. The results are shown in Tables 3 and 4.

Experiment 1

Measurement of NADH-methemoglobin reductase activity

The NADH-methemoglobin reductase activity was evaluated after diluting the lipid-SFH solution with HEPES buffer (50 mM, pH 7.4, 37° C.). Evaluation of the enzymatic activity per unit hemoglobin was carried out in accordance with the method described in E. Beutler, NADH methemoglobin reductase (NADH-ferricyanide reductase), in: E. Beutler (ed.), Red Cell Metabolism: A Manual of Biochemical Methods, 3rd ed., Grune & Stratton, Inc., Orlando, 1984, pp. 81–83.

In evaluating the NADH-methemoglobin reductase activity within the hemoglobin-encapsulating liposomes, the liposome membrane was solubilized with a nonionic surfactant, octylglycopyranoside. The evaluation was carried out as in the case of the solution before the liposomerization.

TABLE 3

| | Reductase activity, L.U./gHb | | |
|---|---|---|---|
| | Before liposomerization with Microfluidizer | After liposomerization with Microfluidizer | Residual activity, % |
| 1 | 13.8 | 13.1 | 94.9 |
| 2 | 12.5 | 13.8 | 110.6 |
| 3 | 13.5 | 12.8 | 94.8 |
| 4 | 12.9 | 11.2 | 86.8 |
| 5 | 13.9 | 15.4 | 110.8 |
| Mean | 13.34 ± 0.62 | 13.24 ± 1.53 | 99.6 |

Experiment 2

Measurement of malate dehydrogenase activity

The malate dehydrogenase activity was evaluated after diluting the lipid-SFH solution with HEPES buffer (50 mM, pH 7.4, 37° C.). Evaluation of the enzymatic activity per unit hemoglobin was carried out in accordance with the method described in H. U. Bergmeyer, A. F. Smith, and E. Bermth, Malate Dehydrogenase, in: H. U. Bergmeyer (ed.), Methods of Enzymatic Analysis, vol. 3, 3rd English Ed., Verlag Chemie Weinheim, 1986, pp 163–175.

In evaluating the malate dehydrogenase activity within the hemoglobin-encapsulating liposomes, the liposome membrane was solubilized with a nonionic surfactant, octylglycopyranoside. The evaluation was carried out as in the case of the solution before the liposomerization.

TABLE 4

| | Dehydrogenase activity, L.U./gHb | | |
|---|---|---|---|
| | Before liposomerization with Microfluidizer | After liposomerization with Microfluidizer | Residual activity, % |
| 1 | 100.8 | 81.1 | 80.5 |
| 2 | 113.3 | 84.9 | 75.0 |
| 3 | 113.8 | 91.7 | 80.6 |
| 4 | 107.8 | 93.8 | 87.0 |
| 5 | 113.9 | 95.4 | 83.8 |
| Mean | 109.92 ± 5.69 | 89.40 ± 6.10 | 81.4 |

NADH-methemoglobin reductase activity was also measured in accordance with the method described in the above Experiment 1 for liposomes prepared by repeating the procedure of Comparative Example 1 except that no cooling was carried out during the liposomerization using the Warling blender. The NADH-methemoglobin reductase activity measured was as low as 17.9%.

As shown in Tables 3 and 4, the hemoglobin-encapsulating liposomes prepared by using Microfluidizer had residual NADH-methemoglobin reductase activity of 99.6% and residual malate dehydrogenase activity of 81.4. Merits of liposomerization using Microfluidizer is clearly demonstrated by such results. It should be noted that malate dehydrogenase is an enzyme associated with TCA cycle, and is involved in the regeneration of reduced-form coenzyme NAD in the hemoglobin-encapsulating liposomes.

MERITS OF THE INVENTION

As described above, the hemoglobin oxidation with lapse of time is significantly suppressed in the hemoglobin-encapsulating liposomes of the present invention.

Generally, hemoglobin-encapsulating liposomes undergo a decrease or loss in their oxygen-transportation capacity due to oxidation of the hemoglobin into methemoglobin in course of their production or storage. On the contrary, the hemoglobin-encapsulating liposome of the present invention retains its excellent oxygen-transportation capacity since the hemoglobin is protected from its irreversible oxidation. Therefore, the hemoglobin-encapsulating liposome of the present invention has properties well suited for an artificial erythrocyte.

We claim:

1. A hemoglobin-encapsulating liposome comprising
   a liposome comprising a lipid,
   a hemoglobin-containing solution encapsulated in said liposome, wherein said hemoglobin-containing solution is a concentrated stroma free hemoglobin solution derived from natural erythrocyte, and
   at least one further added material selected from the group consisting of malic acid, oxaloacetic acid, citric acid, isocitric acid, α-ketoglutaric acid, succinyl-CoA, succinic acid, fumaric acid, aspartic acid, pyruvic acid, phosphoenolpyruvic acid, acetyl-CoA, and glutamic acid in an amount sufficient to suppress hemoglobin oxidation.

2. The hemoglobin-encapsulating liposome according to claim 1, wherein said hemoglobin solution has further added thereto an organic phosphate compound selected from the group consisting of inositol hexaphosphate, tetrapolyphosphate, pyridoxal 5'-phosphate, and ATP.

3. The hemoglobin-encapsulating liposome according to claim 2, wherein said organic phosphate compound is inositol hexaphosphate.

4. The hemoglobin-encapsulating liposome according to claim 1, wherein said hemoglobin solution has further added thereto an a tocopherol analogue selected from the group consisting of tocopherol α, tocopherol β, tocopherol γ, and tocopherol δ.

5. The hemoglobin-encapsulating liposome according to claim 1, wherein said hemoglobin-containing solution has further added thereto at least one compound selected from the group consisting of reduced-form nicotinamide adenine dinucleotide (NADH), oxidized-form nicotinamide adenine dinucleotide (NAD), reduced-form nicotinamide adenine dinucleotide phosphate (NADPH), and oxidized-form nicotinamide adenine dinucleotide phosphate (NADP).

6. The hemoglobin-encapsulating liposome according to claim 5, wherein said compound is added in an amount in the range of from 0.1 to 25 mole per 1 mole of the hemoglobin.

7. The hemoglobin-encapsulating liposome according to claim 1, wherein said concentrated stroma free hemoglobin solution derived from natural erythrocyte is obtained by the steps comprising removing platelets, leucocytes and other plasma components from packed red cells, rinsing the obtained erythrocytes, removing stroma components, and concentrating the stroma-free solution by dialysis.

* * * * *

UNITED STATES PATENT AND TRADEMARK OFFICE
CERTIFICATE OF CORRECTION

PATENT NO. : 5,688,526
DATED : November 18, 1997
INVENTOR(S) : Takeshi OKAMOTO et al It is certified that error appears in the above-identified patent and that said Letters Patent is hereby corrected as shown below:

In Column 7, line 36, delete "15meg$\Omega$.C.cm" and insert -- 15meg$\Omega$°C·cm --.

In Column 9, line 53, delete "$\beta$-NADPH.Na$_4$" and insert -- $\beta$-NADPH·Na$_4$ --.

Signed and Sealed this

Seventeenth Day of February, 1998

Attest:

BRUCE LEHMAN

*Attesting Officer*    *Commissioner of Patents and Trademarks*